US00PP12543P2

(12) United States Plant Patent
Meilland

(10) Patent No.: US PP12,543 P2
(45) Date of Patent: Apr. 9, 2002

(54) MINIATURE ROSE PLANT NAMED 'MEIBORCO'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/649,875

(22) Filed: Aug. 28, 2000

(51) Int. Cl.[7] ..... A01H 5/00

(52) U.S. Cl. ..... Plt./122

(58) Field of Search ..... Plt./122, 129

(56) References Cited

U.S. PATENT DOCUMENTS

PP9,973 P * 7/1997 Meilland ..... Plt./122

* cited by examiner

*Primary Examiner*—Howard J. Locker
(74) *Attorney, Agent, or Firm*—Burns, Doane, Swecker & Mathis, L.L.P.

(57) ABSTRACT

A new and distinct variety of rose plant of the dwarf Miniature Class is provided which abundantly forms attractive double dark red blossoms that sometimes appear to be nearly black in coloration. The growth habit is low compact and bushy. Decorative very dense medium green semi-glossy foliage is formed that contrasts nicely with the dark red blossoms. The new variety is well suited for pot forcing under greenhouse growing conditions.

1 Drawing Sheet

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the 'Meikanrou' variety (U.S. Plant Pat. No. 9,973). The male parent (i.e., the pollen parent) was the product of the pollination of the 'Meijikatar' variety (U.S. Plant Pat. No. 4,682) and the 'Ruimered' variety (U.S. Plant Pat. No. 5,770). The parentage of the new variety can be summarized as follows:

'Meikanrou'×('Meijikatar'×'Ruimered').

The seeds resulting from the above pollination were sown and small plants were obtained which were physically and biologically different from each other. Selective study resulted in the identification of a single plant of the new variety.

It was found the new variety of Miniature rose plant of the present invention possesses the following combination of characteristics:

(a) exhibits a low compact and bushy growth habit, (b) forms in abundance attractive double dark red blossoms, (c) forms decorative very dense medium green semi-glossy foliage, and (d) is well suited for pot forcing.

The dark red blossoms sometimes appear to be nearly black and contrast nicely with the dense medium green foliage.

The new variety well meets the needs of the horticultural industry. It is particularly well suited for pot forcing under greenhouse growing conditions to form a distinctive gift plant.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named the 'Meiborco' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were one year of age and were observed during April while growing on their own roots in greenhouses at LeCannet des Maures, Var, France. Dimensions in centimeters are shown at the bottom of the photograph.

FIG. 1—illustrates a specimen of a young shoot;

FIG. 2—illustrates specimens of three floral buds before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower during the course of opening;

FIG. 6—illustrates a specimen of an open flower—plan view—reverse;

FIG. 7—illustrates a specimen of an open flower—plan view—obverse;

FIG. 8—illustrates a specimen of a fully open flower—plan view—reverse;

FIG. 9—illustrates a specimen of a fully open flower—plan view—obverse;

FIG. 10—illustrates a specimen of a floral receptacle showing the arrangement of the stamens and pistils;

FIG. 11—illustrates a specimen of a floral receptable showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The terminology which precedes reference to the chart has been added in some instances to indicate the corresponding colors in more common terms. The description is based on the observation of six month old specimens of the new variety which were observed during November while growing on their own roots in greenhouses at LeCannet des Maures, Var, France.

Class: Dwarf Miniature.

Plant:

*Height.*—Approximately 20 to 25 cm. on average at the end of the growing season.

*Habit.*—Bushy.

Branches:

*Color.*—Young stems: near Yellow-Green Group 146A.

*Thorns.*—Size: medium. Quantity: sparse as illustrated. Color: greenish on young stems, near Yellow-Green Group 153C. Configuration: fairly straight and elongated on the upper surface.

Leaves:

*Petioles.*—Upper surface: non-glandular, and near Green Group 139B in coloration. Under surface: smooth.

*Stipules.*—Adnate, pectinate, and rather broad.

*Leaflets.*—Number: 3, 5, and 7 (most often). Shape: with a symmetrical tip and a generally obtuse base (as illustrated). Texture: consistent. Serration: regular. General appearance: very dense, medium green and semi-glossy. Color (young and mature foliage): Upper surface: near Yellow-Green Group 144A. Under surface: near Green Group 138A.

Inflorescence:

*Number of flowers.*—Commonly approximately 2 to 5 per stem.

*Peduncle.*—Short, rigid, smooth, near Yellow-Green Group 144A, and the length commonly is approximately 2.5 to 3 cm on average.

*Sepals.*—Upper surface: greenish, near Yellow-Green Group 144B and 144C. Under surface: near Yellow-Green Group 144A. Shape: with weak extensions.

*Buds.*—Shape: conical. Size: small for class, and approximately 1 cm in length.

*Flower.*—Form: double and cup-shaped.

*Diameter: approximately* 3 cm on average when fully open. Color (when opening begins): Upper surface: near Cardinal Red, Red Group 53A and darker. Under surface: near Cardinal Red, Red Group 53A. Color (when blooming): Upper surface: near Currant Red, Red Group 46A and lightly suffused with Red Group 53A. Under surface: near Currant Red, Red Group 46A and lightly suffused with Red Group 53A. Color (at end of opening): Upper surface: near Currant Red, Red Group 46A and lightly suffused with Red Group 53A. Under surface: near Currant Red, Red Group 46A and lightly suffused with Red Group 53A. Fragrance: none. Anthers: near Yellow-Orange Group 17D in coloration. Stamen number: approximately 18 on average. Filaments: near Yellow-Orange Group 17D in coloration. Pistil number: approximately 22 on average. Petal configuration: wedge-shaped base and a reflexed tip. Stigmas: whitish in coloration. Styles: near Red Group 46D. Receptacle: medium green, near Yellow-Green Group 144A, and in longitudinal section in the shape of a pitcher. Lasting quality: long, approximately 10 days on the plant. Petal drop: good, the petals detach well.

Development:

*Vegetation.*—Medium.

*Blooming.*—Very abundant.

*Resistance to diseases.*—Medium.

*Aptitude to bear fruit.*—None.

I claim:

1. A new and distinct variety of Miniature rose plant characterized by the following combination of characteristics:

(a) Exhibits a low compact and bushy growth habit, (b) Forms in abundance attractive double dark red blossoms, (c) Forms decorative very dense medium green semi-glossy foliage, and (d) Is well suited for pot forcing;

substantially as herein shown and described.

* * * * *

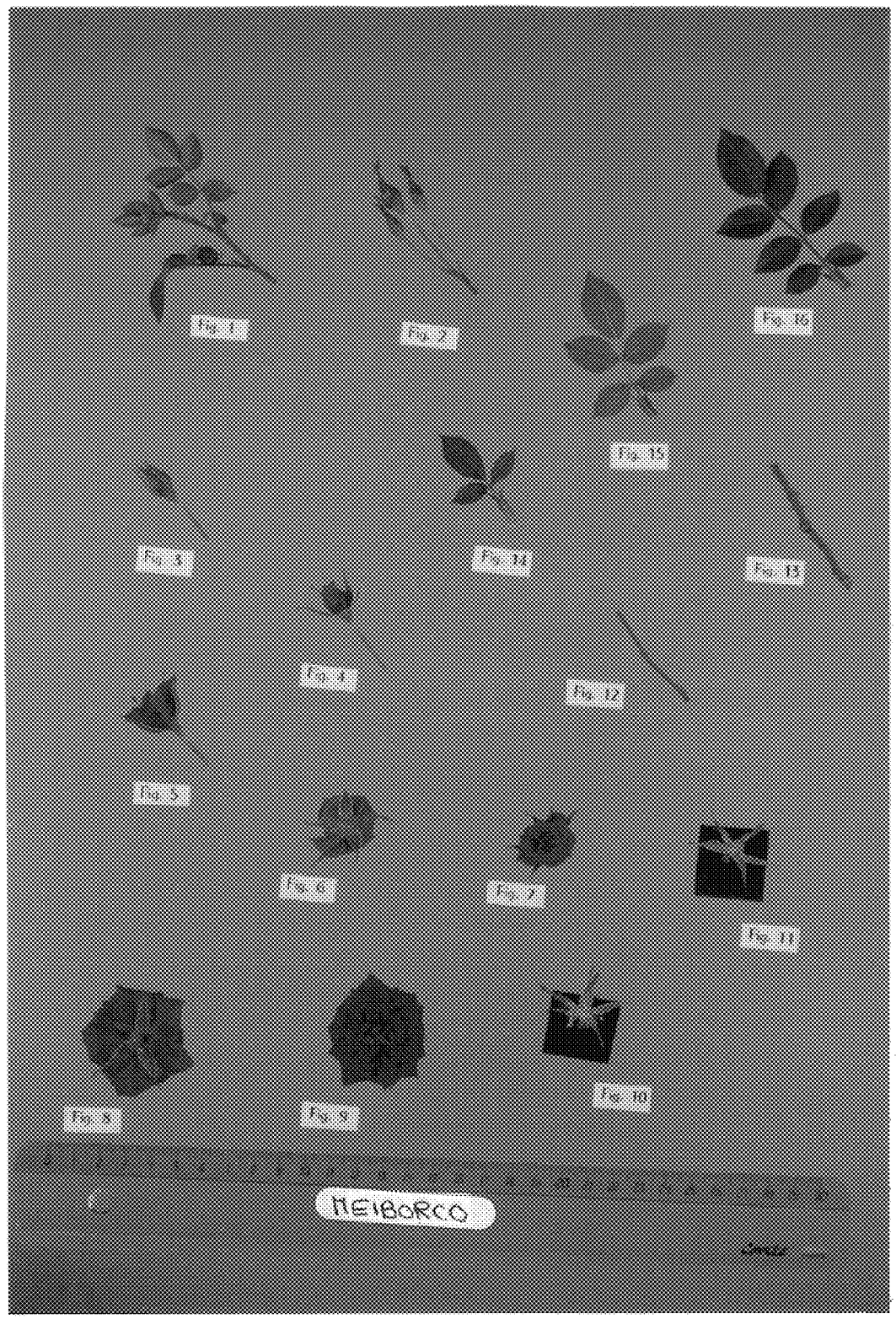
NEIBORCO